(12) United States Patent
Kim

(10) Patent No.: US 11,839,758 B2
(45) Date of Patent: *Dec. 12, 2023

(54) MULTICHANNEL POSTURE DEPENDENT TEMPLATE BASED RHYTHM DISCRIMINATION IN A WEARABLE CARDIOVERTER DEFIBRILLATOR

(71) Applicant: WEST AFFUM HOLDINGS DAC, Dublin (IE)

(72) Inventor: Jaeho Kim, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,378

(22) Filed: May 27, 2022

(65) Prior Publication Data

US 2022/0280774 A1 Sep. 8, 2022

Related U.S. Application Data

(63) Continuation of application No. 16/712,208, filed on Dec. 12, 2019, now Pat. No. 11,344,718.

(51) Int. Cl.
*A61N 1/04* (2006.01)
*A61N 1/39* (2006.01)
(Continued)

(52) U.S. Cl.
CPC .............. *A61N 1/046* (2013.01); *A61B 5/024* (2013.01); *A61B 5/1116* (2013.01); *A61B 5/35* (2021.01);
(Continued)

(58) Field of Classification Search
CPC .... A61N 1/046; A61N 1/3904; A61N 1/0484; A61B 5/024; A61B 5/35; A61B 5/1116;
(Continued)

(56) References Cited

U.S. PATENT DOCUMENTS 3,724,355 A 4/1973 Busch et al.
4,583,524 A 4/1986 Hutchins
(Continued)

FOREIGN PATENT DOCUMENTS

DE 2005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Catherine M Voorhees
(74) *Attorney, Agent, or Firm* — Christensen O'Connor Johnson Kindness PLLC

(57) ABSTRACT

Embodiments of a wearable cardioverter defibrillator (WCD) system include a support structure for wearing by an ambulatory patient, a posture detector and at least one processor. When worn, the support structure maintains electrodes on the patient's body, and using the posture detector and the patient's ECG received via the electrodes, the processor determines the patient's posture, formulates posture-based templates of QRS complexes, and the patient's heart rate. The processor can use these determinations to distinguish between VT and SVT and make no-shock, and shock decisions.

20 Claims, 11 Drawing Sheets

(51) Int. Cl.
   *A61B 5/11* (2006.01)
   *A61B 5/35* (2021.01)
   *A61B 5/00* (2006.01)
   *A61B 5/024* (2006.01)

(52) U.S. Cl.
   CPC .......... *A61B 5/7264* (2013.01); *A61N 1/0484* (2013.01); *A61N 1/3904* (2017.08); *A61B 5/02405* (2013.01)

(58) Field of Classification Search
   CPC ... A61B 5/7264; A61B 5/02405; A61B 5/361; A61B 5/366
   See application file for complete search history.

(56) References Cited

U.S. PATENT DOCUMENTS

| | | | |
|---|---|---|---|
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A * | 9/1994 | Bornn | A61B 5/411 379/38 |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,295,852 B1 | 3/2016 | Williamson | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2005/0154421 A1 | 7/2005 | Ousdigian | |
| 2006/0173499 A1 | 8/2006 | Hampton et al. | |
| 2008/0312709 A1 | 12/2008 | Vollpe et al. | |
| 2009/0005827 A1 | 1/2009 | Weintraub et al. | |
| 2010/0007413 A1 | 1/2010 | Herleikson | |
| 2010/0121209 A1 | 5/2010 | Cazares et al. | |
| 2010/0280841 A1 * | 11/2010 | Dong | G16H 15/00 607/30 |
| 2010/0298899 A1 | 11/2010 | Donnelly et al. | |
| 2011/0022105 A9 | 1/2011 | Owen et al. | |
| 2011/0106194 A1 | 5/2011 | Wang et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |

(56) References Cited

U.S. PATENT DOCUMENTS

| | | |
|---|---|---|
| 2016/0022166 A1 | 1/2016 | Stadler et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0072202 A1 | 3/2017 | Kane et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0282823 A1 | 9/2019 | Freeman et al. |
| 2019/0321650 A1 | 10/2019 | Raymond et al. |
| 2019/0329055 A1 | 10/2019 | Briscoe et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

Life Vest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

\* cited by examiner

SAMPLE COMPONENTS OF WEARABLE CARDIOVERTER DEFIBRILLATOR (WCD) SYSTEM

*SAMPLE COMPONENTS OF EXTERNAL DEFIBRILLATOR*

COMPONENTS OF SAMPLE WCD SYSTEM

*MULTIPLE ELECTRODES FOR SENSING ECG SIGNALS ALONG DIFFERENT VECTORS*

*SOME PERTINENT COMPONENTS FOR SVT/VT DISCRIMINATION IN AN EXAMPLE EXTERNAL DEFIBRILLATOR*

$$r = r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

MULTICHANNEL POSTURE DEPENDENT TEMPLATE BASED RHYTHM DISCRIMINATION IN A WEARABLE CARDIOVERTER DEFIBRILLATOR

CROSS REFERENCE TO RELATED PATENT APPLICATIONS

This patent application is a continuation of U.S. patent application Ser. No. 16/712,208, entitled "MULTICHANNEL POSTURE DEPENDENT TEMPLATE BASED RHYTHM DISCRIMINATION IN A WEARABLE CARDIOVERTER DEFIBRILLATOR," filed Dec. 12, 2019 and may be related to U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE," filed Nov. 2, 2016; U.S. patent application Ser. No. 15/863,551 entitled "WEARABLE CARDIOVERTER DEFIBRILLATOR HAVING ADJUSTABLE ALARM TIME," filed Jan. 5, 2018; U.S. patent application Ser. No. 16/392,541 entitled "WEARABLE MEDICAL (WM) SYSTEM MONITORING ECG SIGNAL OF AMBULATORY PATIENT FOR HEART CONDITION," filed Apr. 23, 2019; and U.S. patent application Ser. No. 16/554,410 entitled "METHODS AND SYSTEMS FOR DISTINGUISHING VT FROM VF," filed Mar. 27, 2019, all of which are incorporated herein by reference in their entirety.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and thus save the patient's life.

All subject matter discussed in this Background section of this document is not necessarily prior art and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description gives instances of cardiac monitoring systems (e.g., WCD systems), devices, systems, storage media that may store programs, and methods.

In embodiments, a cardiac monitoring system includes a support structure for wearing by an ambulatory patient. When worn, the support structure maintains electrodes on the patient's body. The ECG signal(s) can be analyzed to distinguish between supraventricular tachycardia (SVT) and ventricular tachycardia (VT) and VF. In embodiments, the analysis can use heart rate measurements (which can be determined from the ECG signal or signals), widths or durations of the QRS complexes, and consistency of the QRS complexes. In some embodiments, one or more signals in addition to ECG signals are used determine whether the wearer has an arrhythmia. For example, the additional one or more signals may be selected from a set including motion signals, heart sound signals, and/or transthoracic impedance signals.

In a further enhancement, in WCD embodiments, distinguishing between SVT and VT and VF can be used to make a shock/no shock decision. In some embodiments, the WCD distinguishes between SVT and VT using templates derived from the WCD wearer's ECG. In some embodiments, different templates are derived depending on the wearer's posture. In some embodiments, different treatments may be provided to the WCD wearer for SVT compared to VT.

DETAILED DESCRIPTION

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
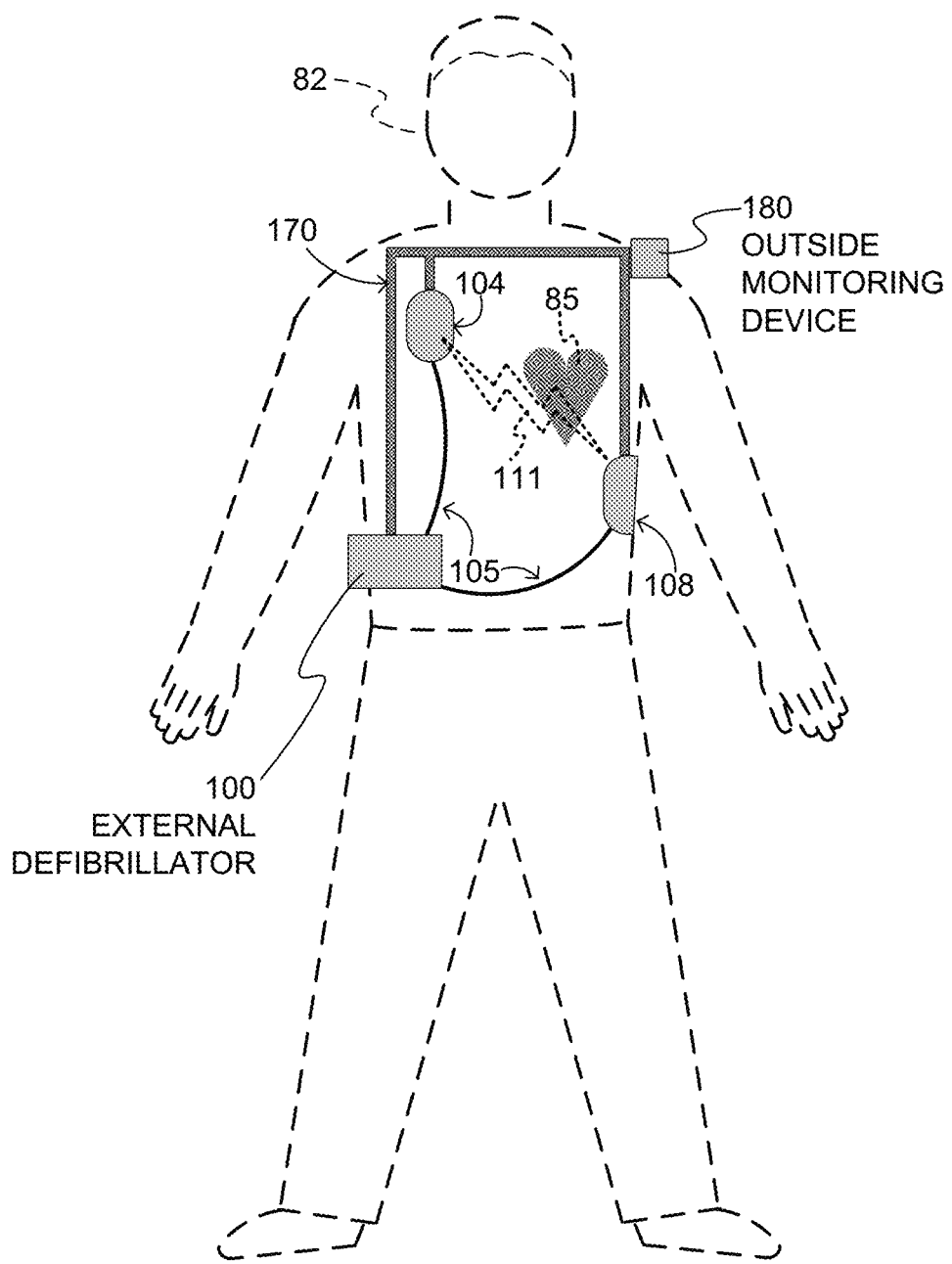
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
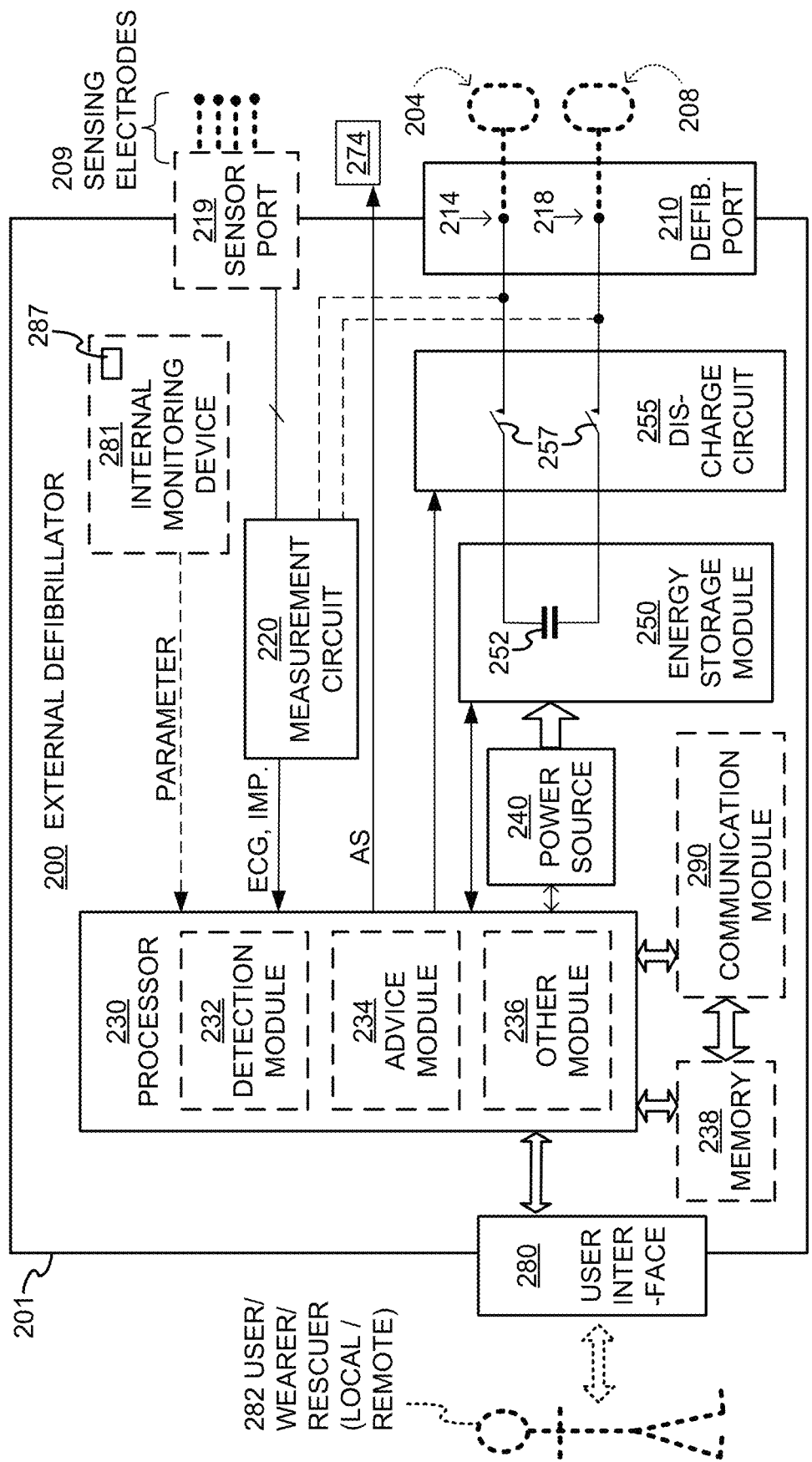
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus may be also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. Published Patent App. Pub. No. 20140043149A1 entitled "MOBILE COMMUNICATION DEVICE & APP FOR WEARABLE DEFIBRILLATOR SYSTEM". This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads.

Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
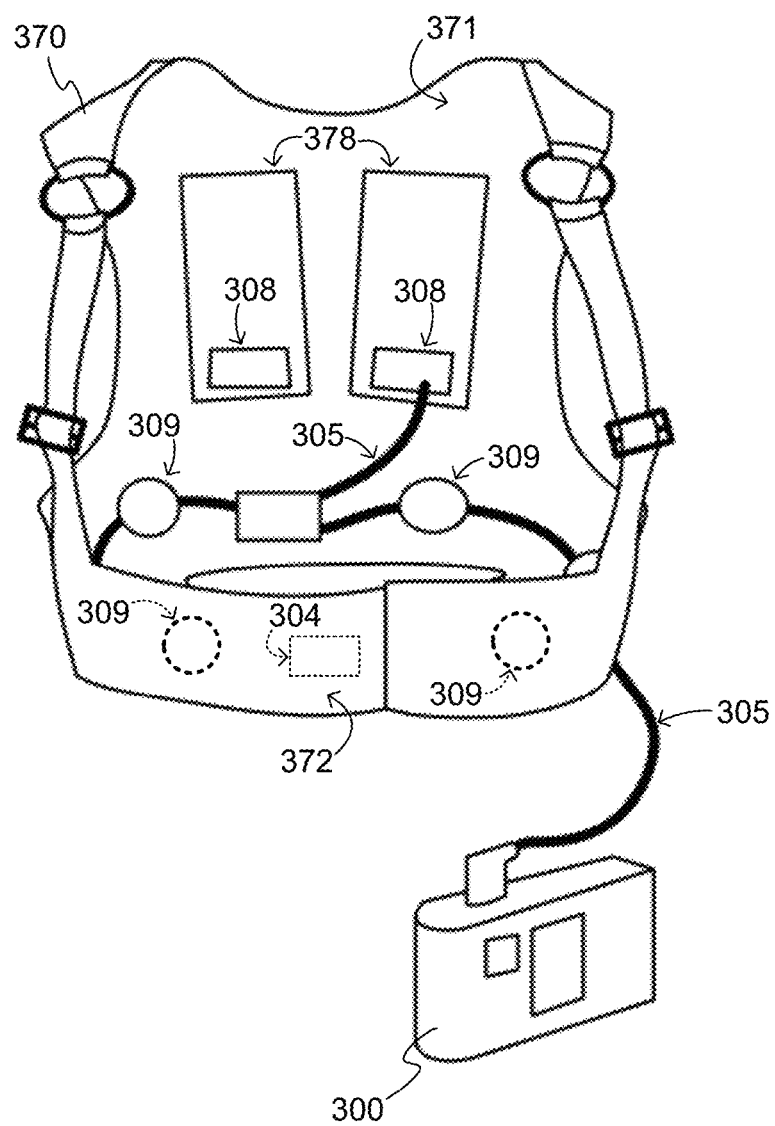
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
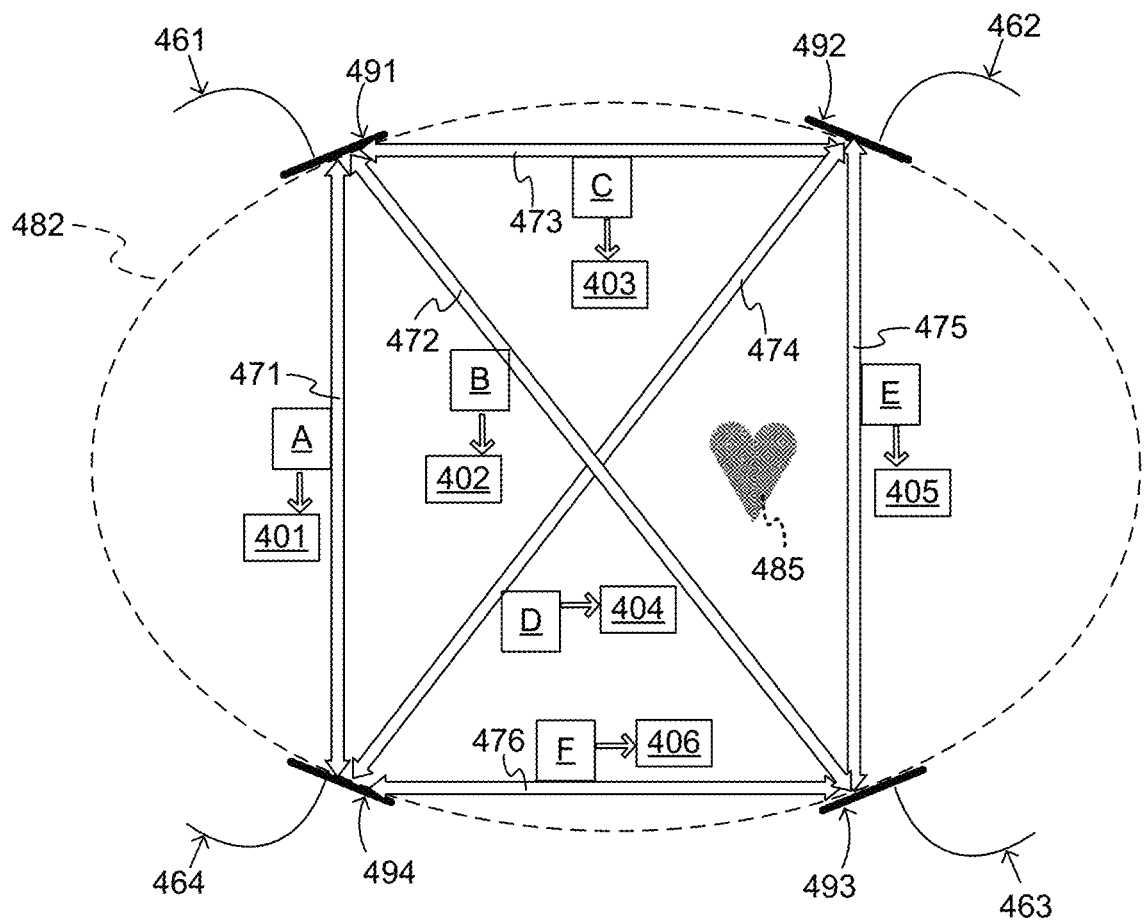
FIG. 4 is a conceptual diagram illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/ NO SHOCK DETERMINATION FROM TWO OR MORE ECG SIGNALS", which is incorporated herein by reference.

Figures 5, 6:
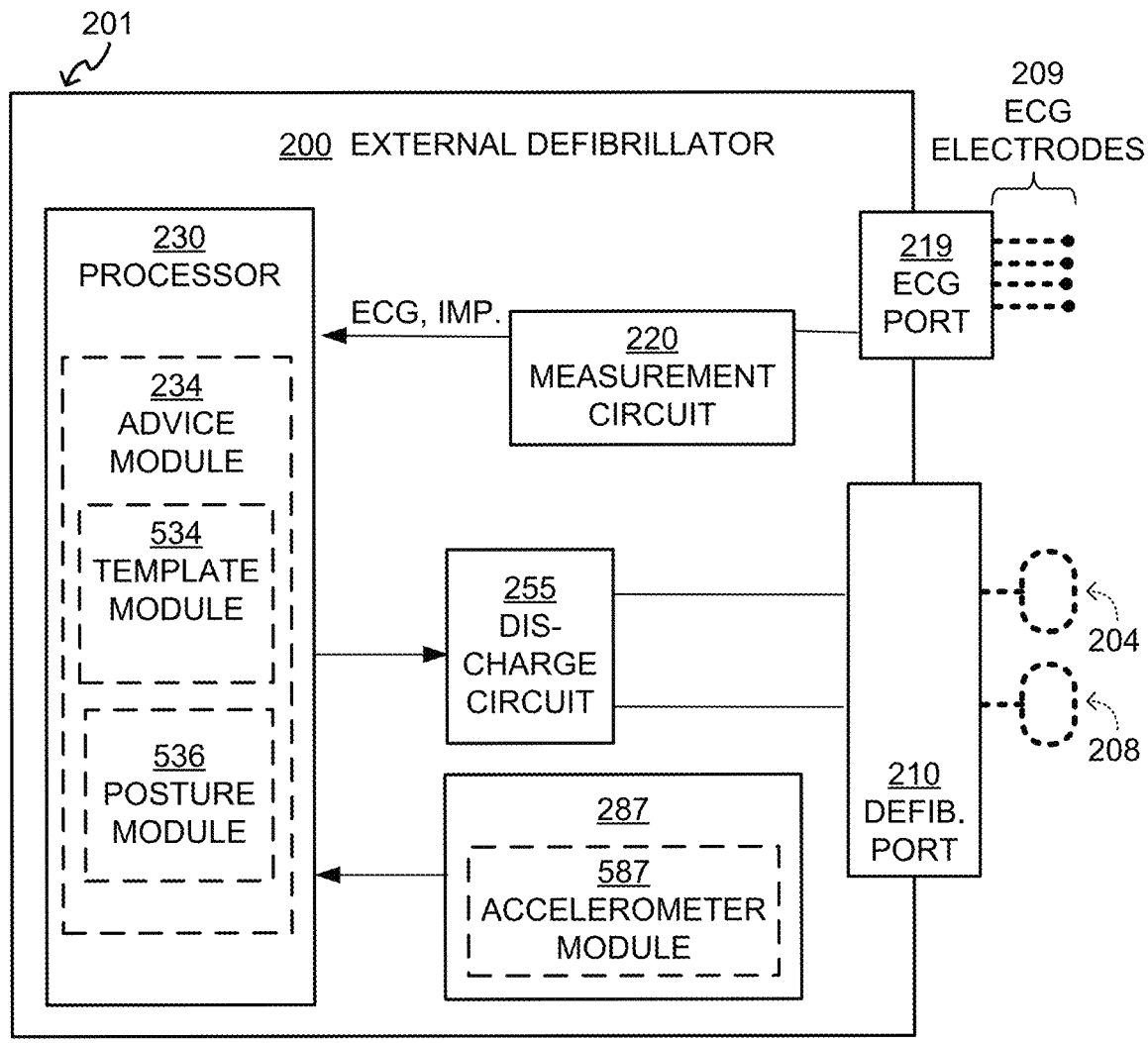
FIG. 5 is a diagram showing some of the components used for VT/SVT discrimination in an example external defibrillator, according to embodiments.
FIG. 6 shows a sample mathematical equation used in determining QRS similarity, according to embodiments.

FIG. 5 is a diagram showing some of the components used for VT/SVT discrimination using templates in an example external defibrillator, according to embodiments. For example, the external defibrillator may be a WCD in some embodiments. While external defibrillator 200 in FIG. 5 is based on the diagram of FIG. 2, some of the components not directly used in making a shock/no shock decision are omitted in FIG. 5 for clarity. Those components that are shown in FIG. 5, in embodiments, operate as previously described in conjunction with FIG. 2, with additional functionality provided by a template module 534, a posture module 536 and an accelerometer module 587 as part of motion detector 287. In some embodiments, posture module 536 is implemented as described in the previously mentioned and incorporated by reference U.S. patent application Ser. No. 15/863,551 entitled "WEARABLE CARDIOVERTER DEFIBRILLATOR HAVING ADJUSTABLE ALARM TIME" filed on Jan. 5, 2018.

In some embodiments, the advice module 234 is configured to output one or more signals indicative of "shock" or "no shock" outputs based on the heart rate, QRS width determined from the patient's ECG, and "similarity" with one or more posture-based templates. In some embodiments, processor 230 (including advice module 234) detect the QRS complexes in the patient's ECG, determine the patient's HR and determine the QRS widths as described in aforementioned U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE". Other embodiments can have other ways of detecting QRS complexes. Further, in some embodiments processor 230 is configured to control the discharge circuit 255 to provide a cardioversion shock as therapy for VT and a defibrillation shock as therapy for VF. In some embodiments, cardioversion shock is a synchronized shock of lower energy than a defibrillation shock. In some embodiments, template module 534 can also be used to determine templates of ECG parameters for use in other algorithms, and in some other embodiments modules 534 and 536 can be combined in a single module.

In embodiments, advice module 234 can use one or both of template module 534 and posture module 536 in making a shock/no shock decision. As will be described below, template module 534 and posture module 536 can be advantageously used to discriminate between SVT and VT and VF for heart rate-QRS width combinations that can result from these arrhythmias. For example, in some embodiments when SVT is detected, the WCD can issue an alert that is different from those issued for VT and VF. In some embodiments when SVT is detected, the WCD can be configured to measuring AF burden, frequency of SVT, duration of SVT. In some embodiments, the WCD can be configured to not treat SVT because the patient is very likely awake and can ask help if needed. Embodiments of template module 534 and posture module 536 are described in more detail below.

Figure 8:
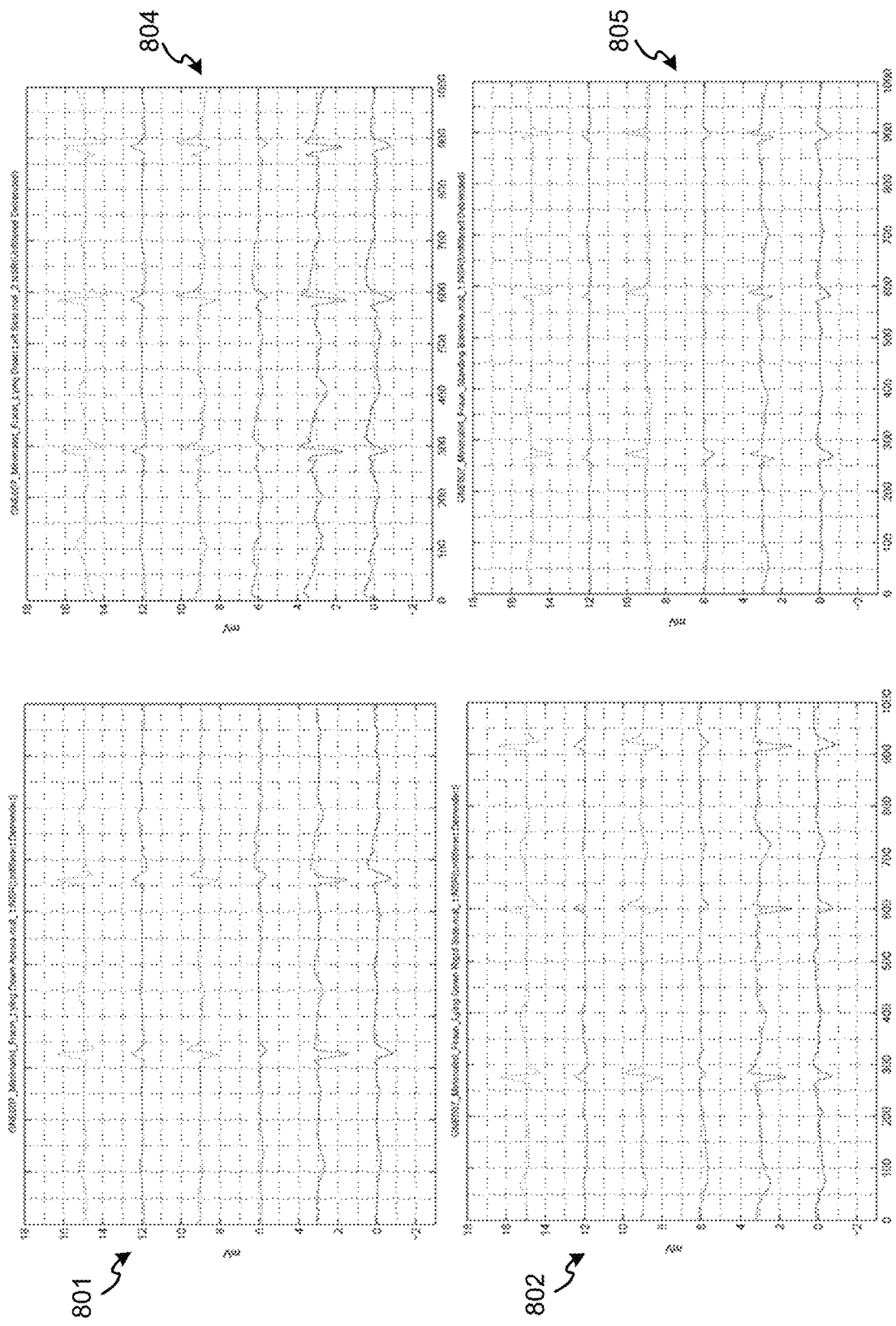
FIG. 8 illustrates examples of ECGs taken while the patient is in different postures.

As shown in FIG. 8, six ECG signals from four different postures (lying down 801, lying on right side 802, lying on left side 804, and standing 805) are different from each other. Some channels show more morphological variation. For example, Channel 1 and channel 6 show that the morphology of standing (right bottom) is different from the morphology of lying on back (left top), lying right (right top) and lying left (left bottom). After review of the present disclosure, it will be appreciated that considering the posture of the patient when analyzing ECG signals can result in more accurately detecting shockable rhythms.

Template Module

To improve the accuracy of detecting shockable from non-shockable arrhythmias, embodiments of the present disclosure use posture dependent templates to better distinguish between shockable and non-shockable (e.g., VT vs SVT) rhythms. Below are described embodiments for formulating templates, but other template formulation techniques can be used in other embodiments.

In some embodiments, a template is formed for each channel (e.g., channels as described above in conjunction with FIG. 4) while the patient is at rest (typically the patient's heart rate will be less than 110 bpm) and in a supraventricular rhythm (which can include normal sinus rhythm (NSR)). In addition to a template per channel, in some embodiments multiple templates are determined or formulated for each channel corresponding to different patient postures as detected by posture module 536. The template(s) can be stored in a buffer of memory 238 (FIG. 2). For example, a template may be formulated at each different posture such as standing, lying on back (supine position), lying on chest (prone position), lying on left side, lying on right side, as detected by the posture module 536.

In some embodiments, a sitting posture is classified as a standing posture. Examples of ECG signals from different postures from multiple channels were previously described in conjunction with FIG. 8.

Template formulation for a particular posture and channel is described in the next few paragraphs, according to some embodiments. The process can be repeated for each of the other channels and postures so that each channel has multiple templates corresponding to multiple patient postures.

The initial beat for template formulation is selected after a regular interval and the following beat after a regular interval is compared with the initial beat. As used herein in this context, a regular interval is an interval longer than the period of a 110 bpm beat; i.e., 545 ms. For example, during bigeminy, only beats after long intervals will be considered. During AF which has large RR interval variability, beats after long intervals are considered. In some other embodiments, the template formulation starts when two regular beats are found to be similar (which can delay the start of the template formulation). In some embodiments, when any two beats are not "similar", these two beats can be considered as candidate templates. The beats following these two beats are compared to the candidate templates and templates can be formed as described above. In some embodiments, the beats are aligned in time, for example, by detecting the larger of a positive or negative peak of the beat, and a few samples before and after the peak point are tried to get a best alignment. Once the beat is aligned with the initial beat, the "similarity" of the beats is determined. In some embodiments, the similarity is determined using a sample correlation coefficient (SCC) algorithm.

FIG. 6 shows a sample SCC algorithm used in determining beat similarity, according to embodiments. In some embodiments, the patient's ECG signal is received by processor 230 via measurement circuit 220, ECG port 219 and ECG electrodes 209. The ECG signal is sampled (e.g. by measure circuit 220 or processor 230). The samples of beats (i.e., the samples of the ECG signal corresponding to QRS complexes) are identified and formed into datasets. For example, one dataset includes n samples of a beat sensed from a channel; i.e., $\{x_1, x_2, \ldots x_n\}$ and represents the initial beat (described above). A second data set includes n samples of another beat sensed from the same channel; i.e., $\{y_1, y_2, \ldots y_n\}$ and represents the following beat. The mean of both data sets (i.e., $\bar{x}$, $\bar{y}$) are determined by template module 534. In some embodiments, the similarity or correlation between the two beats can then be determined by template module 534 using the algorithm of FIG. 6.

In some embodiments, if the similarity exceeds a threshold (i.e., are substantially similar), the 2 beats are combined to serve as the template. In some embodiments the beats are combined by taking the mean of corresponding samples of the beats. Other embodiments take the median of the corresponding samples, and still other embodiments use a weighted average of corresponding samples. In some embodiments, the threshold is 0.9, but in other embodiment the threshold can range from 0.85 to 0.95.

In some embodiments, N similar beats are used to form the template (N being a positive integer; for example, N is 20 in some implementations). However, if M (M being a positive integer; for example, M is 60 in some implementations) successive beats after the initial beat are compared without finding N similar beats to combine, then the template formation is skipped. In other embodiments, the number of beats N used to form a template can range from 10 to 30, and the number of successive beats M without finding the N beats can range from 30 to 90. Further, as previously described, in some embodiments, this template formation process is performed for multiple postures for each channel.

In some embodiments, the template is updated by performing the same process described above to form the template, using the existing template as the "initial" template. The template is updated on a daily basis in some embodiments; however, in other embodiments, the template can be updated at different intervals such as, for example, on an hourly basis, or every two hours, or every four hours, etc. In some embodiments, rather than immediately updating the template after receiving the beats, the beats can be captured and stored in memory for SSC calculation and template updating at a later time. Further, in some embodiments the templates are stored in a non-volatile memory of the WCD so that a temporary power interruption (e.g., when changing the WCD battery) does not result in loss of the templates. Still further, in some embodiments the templates can be transmitted to a remote server and can be reloaded into the WCD when needed. In a further refinement, captured beats can be transmitted and stored at the remote server for "off-line" template formulation and SCC calculation.

In some embodiments, the ECG samples used in template formulation are the ECG samples used in the rhythm analysis. However, in other embodiments, the samples used for template formulation can be at a lower "rate". For example, the ECG samples may be decimated to reduce the effective rate, while in some other embodiments, only the samples corresponding to key features (e.g., peaks, valleys, and baseline) are used in template formulation.

Figure 7:
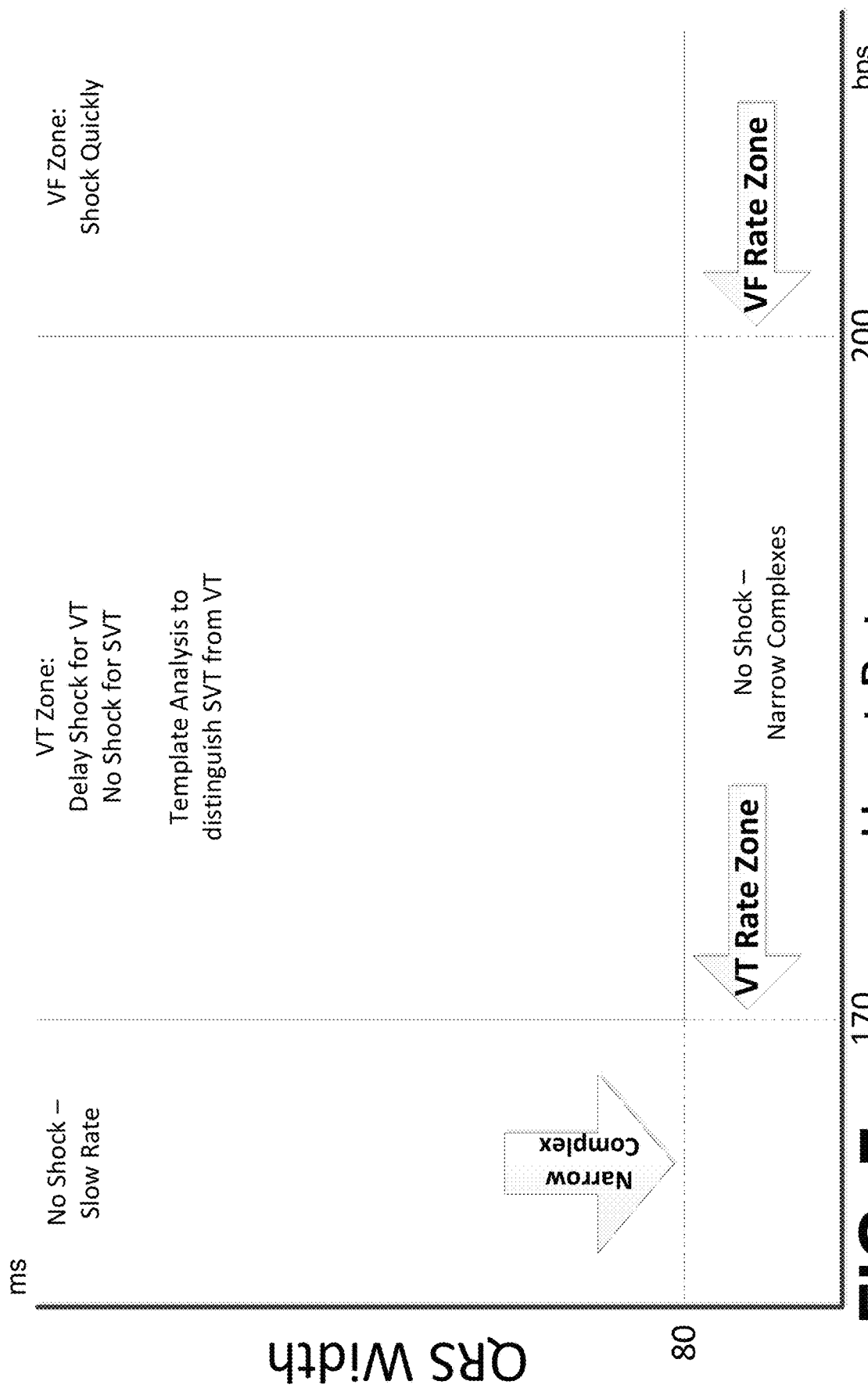
FIG. 7 is a diagram illustrating zones corresponding to VT and VF decisions based on QRS width and heart rate, according to embodiments.
Figure 10:
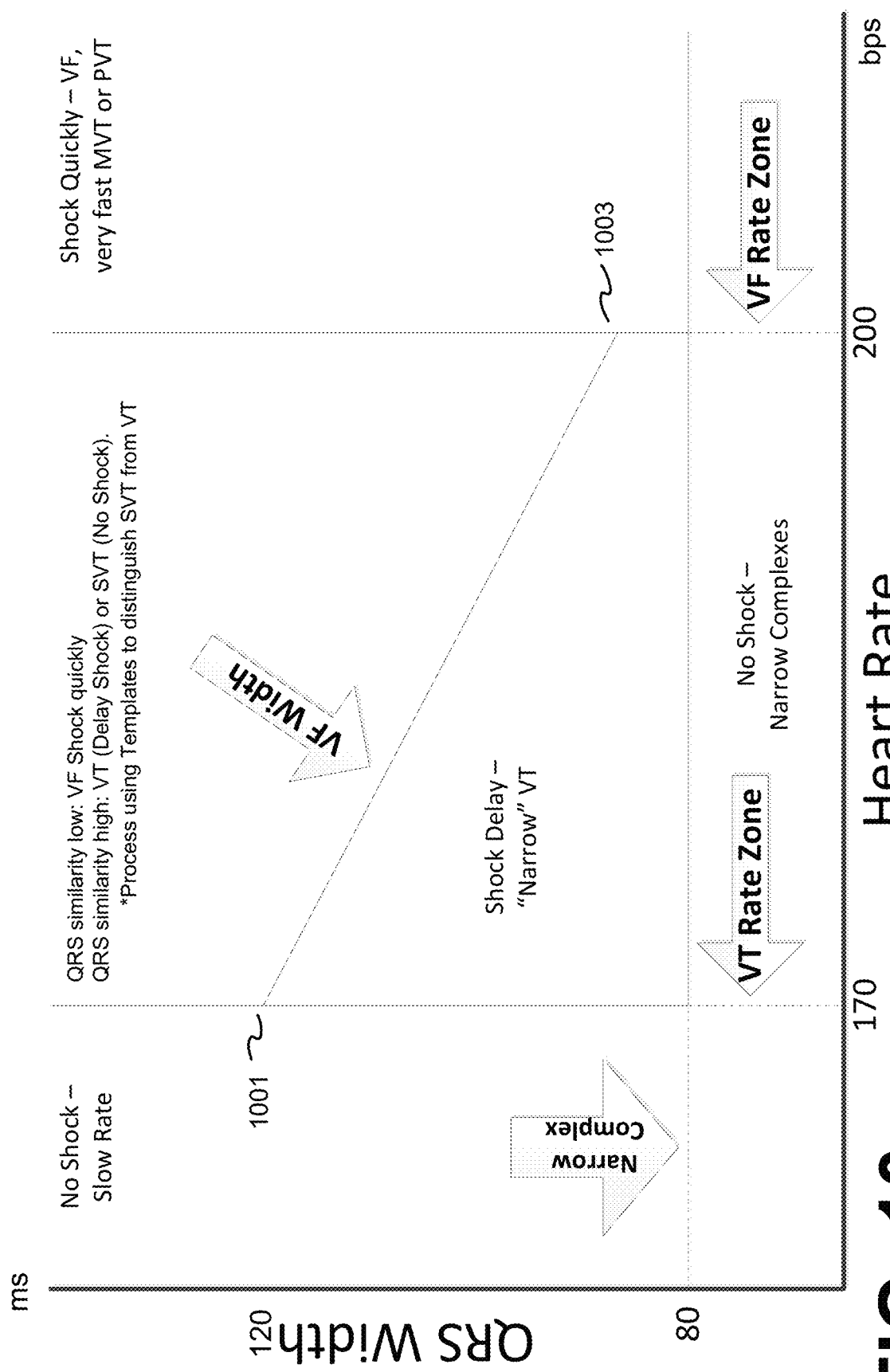
FIG. 10 is a diagram illustrating zones corresponding to VT and VF decisions based on QRS width, heart rate and QRS consistency, according to embodiments.

FIG. 7 illustrates zones corresponding to VT and VF decisions based on QRS width and heart rate, according to embodiments. In the FIG. 7 example, the VT zone is between 170 and 200 bps and QRS width greater than 80 ms. Similarly, FIG. 10 illustrates zones corresponding to VT and VF decisions based on QRS width, heart rate and QRS consistency, according to embodiments. In some embodiments, QRS similarity can be determined as described in aforementioned U.S. patent application Ser. No. 16/554,410 entitled "METHODS AND SYSTEMS FOR DISTINGUISHING VT FROM VF. In the FIG. 10 example, the VT zone is between 170 and 200 bps, but the VF width line and QRS similarity are used instead of QRS width. The zone between the heart rate thresholds and below the VF width line is part of the VT zone, along with rhythms above the VF width line with high similarity.

In accordance with embodiments of the present disclosure, beats falling in the VT zone may be analyzed using templates to distinguish non-shockable from shockable rhythms (e.g., SVT from VT). In other embodiments, the VT zone may be defined with different QRS widths and/or heart rates than shown in FIGS. 7 and 10, and further, in some other embodiments the VT zone may be defined using heart rates without considering QRS width.

Further, some WCDs use heart rates to determine a VT zone, and use vectorcardiograms templates to distinguish shockable from non-shockable rhythms. In accordance with embodiments of the present disclosure, vectorcardiogram templates are formulated for the patient in different postures.

Beat Classification

For a posture (e.g., detected by posture module 536 of FIG. 5), if a template for that posture has been formulated, the advice module 234 (FIG. 5) classifies a received beat as follows. In some embodiments, if the SCC reaches a "high" threshold (e.g., 0.95) indicating the beat is substantially similar to the template, then the advice module 234 (FIG. 5) determines that the beat is SVT. On the other hand, if the SCC is below a "low" threshold (e.g., 80) indicating the beat is substantially dissimilar to the template, then the advice module 234 (FIG. 5) determines that the beat is VT. However, if the SCC is between the two thresholds, the advice module 234 determines that the beat is "indeterminate".

The morphology during supraventricular rhythms or normal sinus rhythm (NSR) can change due to the posture change or electrode location shift relative to the heart. For example, if the SCC of each beat during template formulation was consistently greater than 0.95, then the "high" threshold can be set to 0.95, or even slightly higher. However, if the SCC varied from 0.9 to over 0.95, then in some embodiments the "high" threshold can be set to 0.9. Still further, in some embodiments, if no template was formulated for the current posture and channel, a template for a different posture in the same channel may be used and the "high" threshold can be reduced (e.g., from 0.95 to 0.9). In some other embodiments, the "high" threshold is not changed which would tend to result in more "indeterminate" classifications.

In some embodiments, for each channel the advice module 234 (FIG. 5) is configured to classify the beats in groups of 10 and then apply a majority rule to determine the rhythm. So, if the group of 10 beats is classified to have 4 SVT beats, 3 VT beats, and 3 indeterminate beats, the advice module 235 determines the rhythm as SVT. The size of the group need not be 10. For example, in some embodiments that group size may range from 10 to 30.

In other embodiments, for each channel the advice module 234 (FIG. 5) is configured to classify each group of beats and then determine the percentage of the beats in the group that were classified as SVT. If the percentage exceeds a preselected percentage (e.g., 40 percent), then the rhythm is determined to be SVT.

In some embodiments, the WCD system "qualifies" each channel. For example, noisy channels may not be qualified. When only one channel is qualified, the rhythm determined by the one qualified channel is the "final" rhythm and used by the advice module 234 (FIG. 5) to make a shock decision.

In some embodiments, when two channels are qualified, if at least one channel is determined as VT, the final rhythm is VT.

When three channels are qualified, Table 1 below is used to determine the final rhythm, according to some embodiments.

TABLE 1

| Conditions | Final Rhythm |
| --- | --- |
| Two channels are SVT | SVT |
| Two channels are VT | VT |
| One VT and one/two indeterminate | VT |
| One SVT and two indeterminate | SVT |
| Three indeterminate | VT |

When four channels are qualified, Table 2 below is used to determine the final rhythm, according to some embodiments. Further, in some embodiments if any of the channels is determined as SVT, the detection duration can be extended, which may help clarify the final rhythm. For example, if some channels are determined as SVT and others as VT, it may be that the VT will self-terminate or is caused by a temporary noise condition. For example, sometimes noise on a channel is caused by patient movement, and the noise will be reduced when the patient stops moving.

TABLE 2

| Conditions | Final Rhythm |
|---|---|
| Three channels are SVT | SVT |
| Two SVT and one/two indeterminate | SVT |
| At least two channels are VT | VT |
| One VT and two/three indeterminate | VT |
| One SVT and three indeterminate | SVT |
| Four indeterminate | VT |

In some embodiments, the best channel can be selected for template matching and rhythm decision. For example, the best channel may be the channel with the largest signal-to-noise ratio, or the channel with the highest amplitude R-wave, or the channel with beats having the highest self-similarity values, or the channel with the lowest high frequency content, or with the lowest baseline drift.

In some embodiments, two primary channels can be used for template matching and rhythm decision. In such embodiments the rules of Table 2 are used to determine the final rhythm.

In some embodiments, the overall matching of the qualified channels can be used for rhythm decision. In such embodiments, the overall number of SVT beats, VT beats and indeterminate beats are counted, and the majority rule can be used.

In some embodiments, the rhythm determination can be segment-based, while in other embodiments the rhythm determination is real time continuous based. For example, in some real-time continuous embodiments, the rhythm of each channel is updated at each detected beat.

In some embodiments, the WCD can be configured to formulate templates for patients with pacemakers. For example, in some embodiments adapted for pacemaker patients with pacemakers capable of providing continuous pacing such as CRT pacing, the CRT pacing feature is turned off while the WCD is formulating the templates as described above. In other embodiments adapted for pacemaker patients, the WCD is configured to formulate templates while temporarily turning off the pacemaker.

In some embodiments, the WCD is configured with pacing pulse detection. For example, in some embodiments the pacing detection can be implemented using integrated circuit devices with built in pacing detection such as, for example, the ADAS1000 commercially available from Analog Devices with corporate headquarters in Norwood, MA In other embodiments, the pacing detection can be implemented as disclosed in U.S. Pat. No. 5,951,483, for example, with a smaller number of ECG leads. In other embodiments, pacing pulses can be detected by their uniformity of the pacing pulses and pacing rate. In addition, in some embodiments the WCD is configured to generate templates while there are no pacing pulses being detected and the patient's HR is below the maximum pacing rate of the pacemaker. For patients known to have a particular pacemaker implanted, the maximum pacing rate of this pacemaker can be entered into the WCD at the time the WCD is fitted to the patient. Alternatively, the WCD can be configured to formulate templates when no pacing pulses are being detected and the detected HR is slower than the preselected threshold (for example 130 bpm).

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 9:
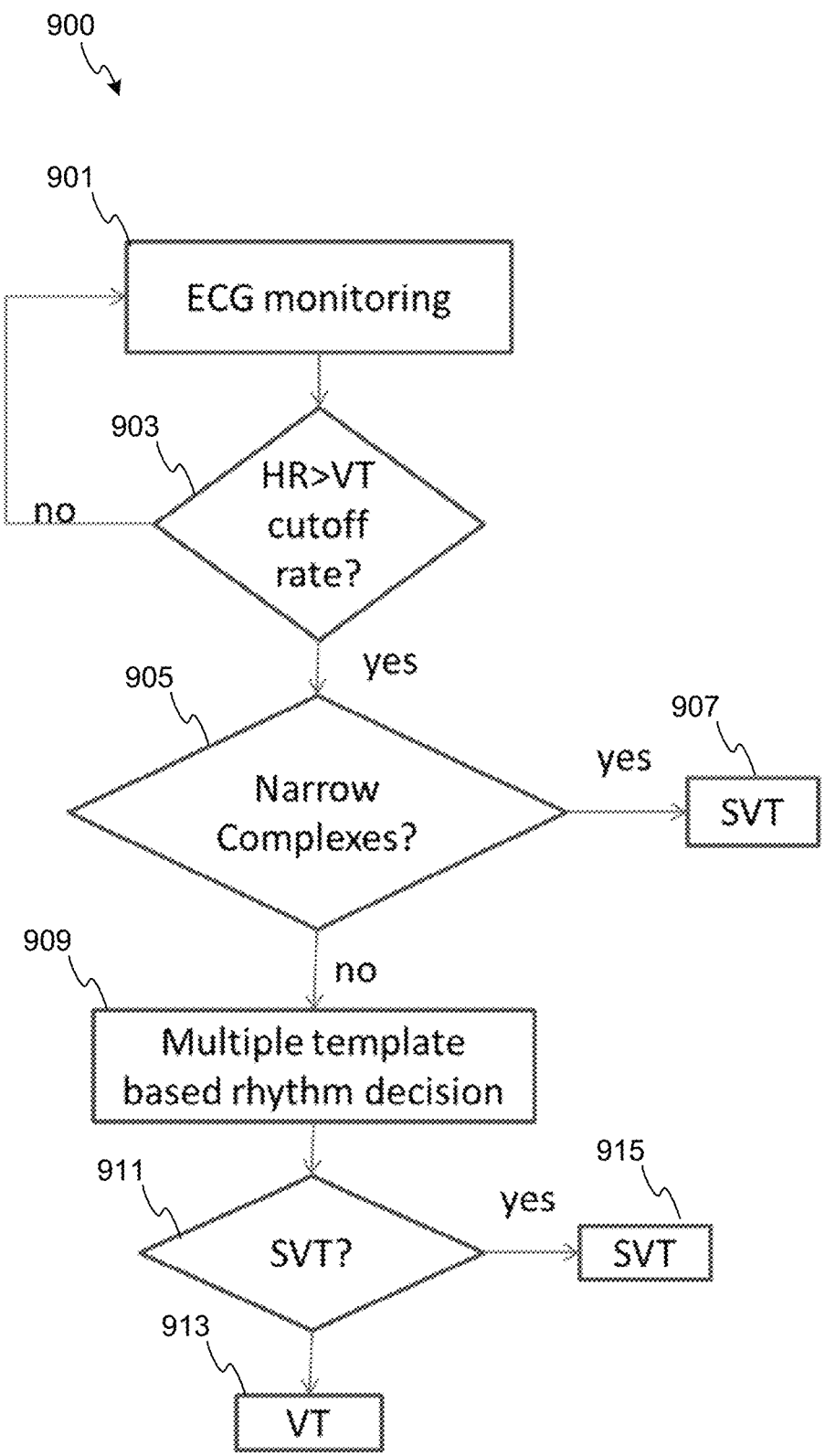
FIG. 9 is a flowchart for illustrating sample methods for distinguishing between VT and SVT, according to embodiments.

FIG. 9 is a flowchart for illustrating an example method 900 for distinguishing between VT and SVT, according to embodiments. In an operation 901, a patient's ECG is monitored. In some embodiments, the patient's ECG is monitored by an external defibrillator such as, for example, the WCD systems of FIGS. 2, 3 and 5. In other embodiments, a wearable monitor is used to monitor the patient's ECG.

In an operation 903 the patient's heart rate (HR) is compared to a VT threshold or cutoff rate. In some embodiments, the patient's HR is determined from the monitored ECG, while in other embodiments the patient's HR is determined using other sensors, such as optical sensors, heart sound sensors, motion sensors, etc. In some embodiments, operation 903 is performed by a processor configured to receive the patient's HR information such as, for example, processor 230 (FIG. 5). In some embodiments, the patient's average HR over a preset period of time (e.g., 5 seconds) is determined and compared to the VT threshold or cutoff rate. In some embodiments, the preset period of time can range from 4 to 15 seconds, or a preset number of HR measurements may be used to determine the average HR for comparison to the VT threshold or cutoff rate. In some embodiments, the heart rate from multiple channels is averaged to determine the average HR, while in other embodiments, a single channel of multiple channels is selected for determining or measuring the patient's HR. In the description below for other operations, the patient's HR may be an average HR determined as described above.

In some embodiments, the patient's HR is compared to a VF threshold (operation not shown). In such embodiments, the VF threshold is higher than the VT threshold and if the patient's HR exceeds the VF threshold then the patient is determined to be experiencing VF. In such embodiments, the operational flow of method 900 proceeds to a defibrillation process (not shown) to administer a shock to the patient. In some embodiments, the defibrillation process can be as described above in conjunction with FIG. 2. To improve the VT and VF classifications, some embodiments also use QRS width thresholds in addition to HR thresholds to define the VT and VF zones, as described in conjunction with FIG. 7, or in aforementioned U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE".

Returning to operation 903, if the patient's HR does not exceed the VT threshold method 900 returns to operation 901. However, if the patient's HR does exceed the VT threshold, operation flow of method 900 proceeds to an operation 905.

In operation 905, the width of the QRS complexes or beats is determined or measured to determine whether the beats or QRS complexes are narrow. In some embodiments, a measurement circuit and/or processor (such as the previously described measurement circuit 220 and processor 230) determine the QRS width. In embodiments, this width is compared to a threshold value and if the width is below this threshold the patient's QRS complexes are determined to be narrow. In some embodiment, this threshold value is 80 ms, but can range from 70 to 140 ms in other embodiments. If the beats or QRS complexes are determined to be narrow, the operational flow proceeds to an operation 907 in which the patient's rhythm is determined or classified as SVT. In some embodiments, operation 907 includes an SVT process in which the SVT detection is logged but no shock is delivered to patients. However, if in operation 905 the beats or QRS complexes are determined to be not narrow, the operational flow proceeds to an operation 909.

In operation 909, the beats are compared to one or more posture-based templates. For example, a processor such as processor 230 (FIG. 5) can be configured to compare the beats to the one or more posture-based templates. In some embodiments the posture-based templates can be formed as described above in conjunction with FIGS. 5 and 6. In some embodiments, the beats are compared to only one posture-based template corresponding to the patient's detected or determined posture. For example, in some embodiments a posture module (such as previously described posture module 536) determines the patient's posture, and a processor (such as processor 230) selects the template corresponding to the determined posture. In some embodiments, the beats are compared to posture-based templates by determining the similarity between the beats and template. For example, the comparison is performed using the SCC or similar algorithm described above in some embodiments.

In an operation 911 the beats are classified as SVT or VT depending on the results of operation 909. For example, a processor such as processor 230 (FIG. 5) can be configured to classify the beats as described above in conjunction with Tables 1 and 2. If the beats are classified as VT, the operational flow proceeds to an operation 913 in which a VT process is performed. In some embodiments, operation 913 includes determining whether the VT is sustained VT as described above, for example, in conjunction with FIG. 7. In some WCD embodiments, if the VT self-terminates within a predetermined time period the WCD does not initiate a shock process (not shown), but if the VT lasts for the predetermined time period the WCD does initiate the shock process.

However, if operation 909 the beats are classified as SVT, the operational flow proceeds to an operation 915 in which an SVT process is performed. In some embodiments, the SVT process of operation 915 can include logging the SVT detection and ensuring no shock is delivered to the patient.

Figure 11:
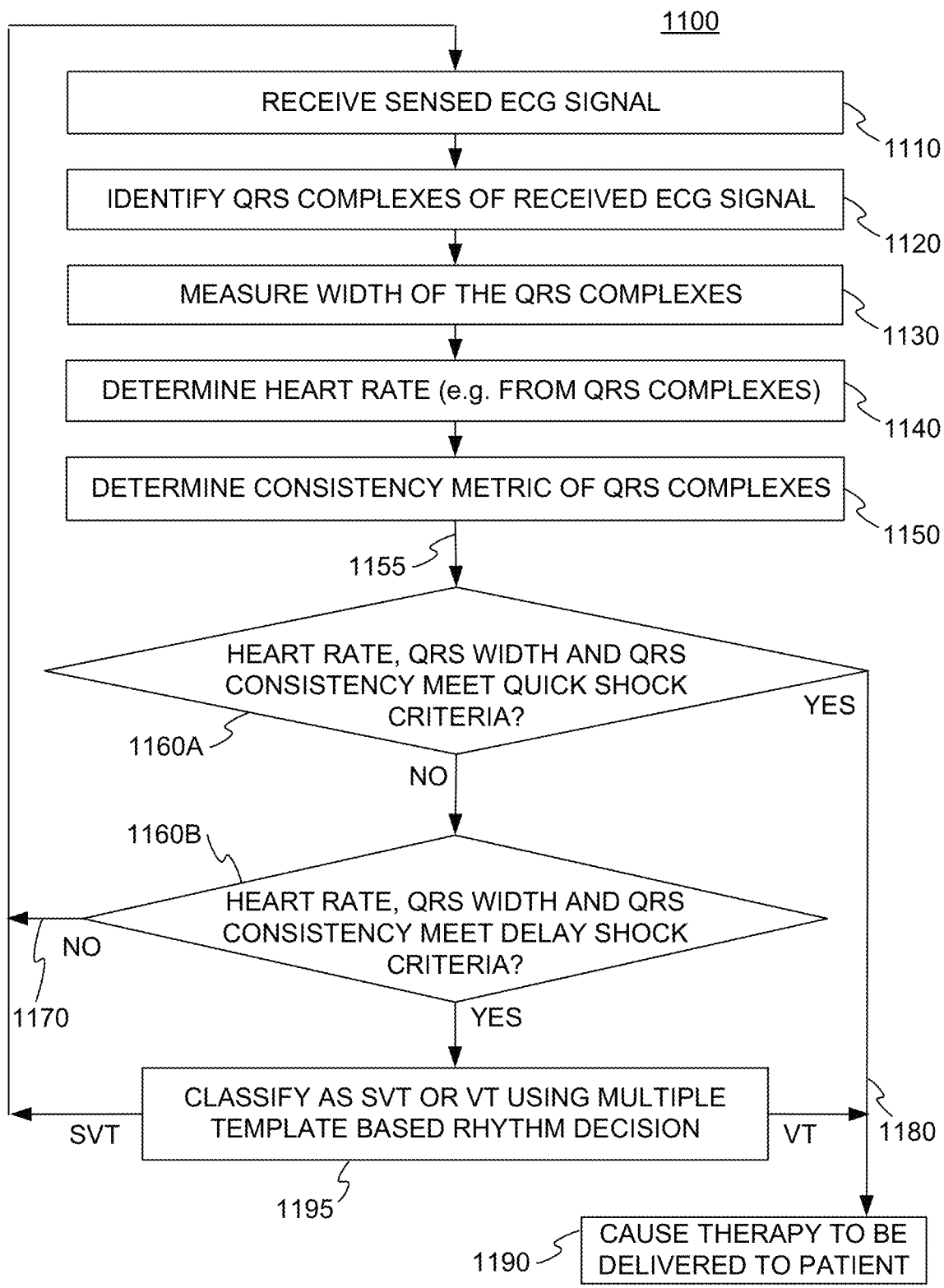
FIG. 11 is a flowchart for illustrating additional sample methods for distinguishing between VT and SVT, according to embodiments.

FIG. 11 is a flowchart for illustrating a method 1100 for distinguishing between VT and SVT using one or more posture-dependent templates and QRS consistency, according to embodiments. In an operation 1110, a patient's ECG signal is received. In some embodiments, the patient's ECG is monitored by an external defibrillator such as, for example, the external defibrillator systems of FIGS. 2, 3 and 5, in which the patient's ECG signal is received via ECG sensors such as, for example, ECG electrodes 209 and measurement circuit 220 (FIGS. 2 and 5). In other embodiments, a wearable monitor is used to monitor the patient's ECG.

In embodiments, the remaining operations illustrated in FIG. 11 can be performed at least in part by a processor such as processor 230 (FIG. 5).

In an operation 1120, QRS complexes or beats in the received ECG signal are identified. In some embodiments, for example, the processor may be configured to detect QRS complexes as described in aforementioned U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE".

In an operation 1130, the widths of the identified QRS complexes is measured. In some embodiments, the processor may be configured to determine the QRS widths. For example, the processor may be configured to determine QRS widths as described in aforementioned U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE".

In an operation 1140, the patient's HR is determined. In some embodiments, the processor can be configured to determine the patient's HR from the QRS complexes (e.g., the inverse of the R-R interval). For example, the processor may be configured to determine HRs as described in aforementioned U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE". In other embodiments, the patient's HR may be determined from other sensors and/or parameters instead of or in addition to the QRS complexes.

In an operation 1150, a consistency metric of the identified QRS complexes is determined. In some embodiments, for example, the processor may be configured to determine the consistency metric as described in aforementioned U.S. patent application Ser. No. 16/554,410 entitled "METHODS AND SYSTEMS FOR DISTINGUISHING VT FROM VF". As indicated by an arrow 1155, operational flow of method 1100 then proceeds an operation 1160A.

In operation 1160A, the HR, QRS width, and QRS consistency from operations 1120-1150 are compared to a "quick shock" criteria. In some embodiments, HR and QRS width thresholds can be used to define VT and VF zones such as illustrated, for example, in FIGS. 7 and 10. In addition, the processor may be configured to compare the HR and QRS width from operations 1140 and 1130 to the quick shock criteria, for example, by determining which zone of FIG. 7 (or FIG. 10) the HR and QRS parameters fall into VF zone (e.g., the upper right zone in FIG. 7 or FIG. 10). Further, in some embodiments, along with posture-based template, a QRS consistency threshold can be used as a factor in distinguishing VT from SVT for rhythms that fall in the VT zone. In some embodiments, the QRS consistency metric is as described in aforementioned U.S. patent application Ser. No. 16/554,410 entitled "METHODS AND SYSTEMS FOR DISTINGUISHING VT FROM VF".

If it is determined that the HR, QRS width and QRS consistency does not meet the quick shock criteria (for example, these parameters fall in the VT zone or the no shock zone on the left side of FIG. 7 or FIG. 10), operation flow proceeds to an operation 1160B. However, if these parameters do meet the quick shock criteria, as indicated by arrow 1180, the operation flow proceeds to an operation 1190 in which a therapy process is initiated to provide therapy (e.g., a defibrillation shock) to the patient.

Returning to operation 1160B, the HR, QRS width, and QRS consistency determined from operations 1120-1150 are compared to a "slow shock" criteria. In some embodiments, for example, if these parameters fall into the VT zone (and not the no shock zone) and the VT does not self-terminate before a predetermined time period, the slow shock criteria is met. If the slow shock criteria are not met, operational flow returns to operation 1110 as indicated by arrow 1170. However, if the slow shock criteria is met, the operation flow proceeds to an operation 1195.

In operation 1195, the QRS complexes or beats are compared to posture-based templates to classify the beats. In some embodiments, the processor is configured to receive sensor data indicative of the patient's posture. For example, the sensor data may be received from an accelerometer module such as accelerometer module 587 (FIG. 5). In addition, the processor may be configured to: (a) formulate the posture-based templates; and (b) classify the beats as SVT or VT, as described above in conjunction with FIGS. 5 and 6. In some embodiments with multiple channels, the processor can classify the beats as described above in conjunction with Tables 1 and 2. Still further, in some embodiments the processor is configured so that if the beats are classified as SVT, a therapy process is not initiated, and the operational flow returns to previously described operation 1110. However, if the beats are classified as VT, the operational flow proceeds to previously described operation 1190 to initiate the therapy process.

Figure 12:
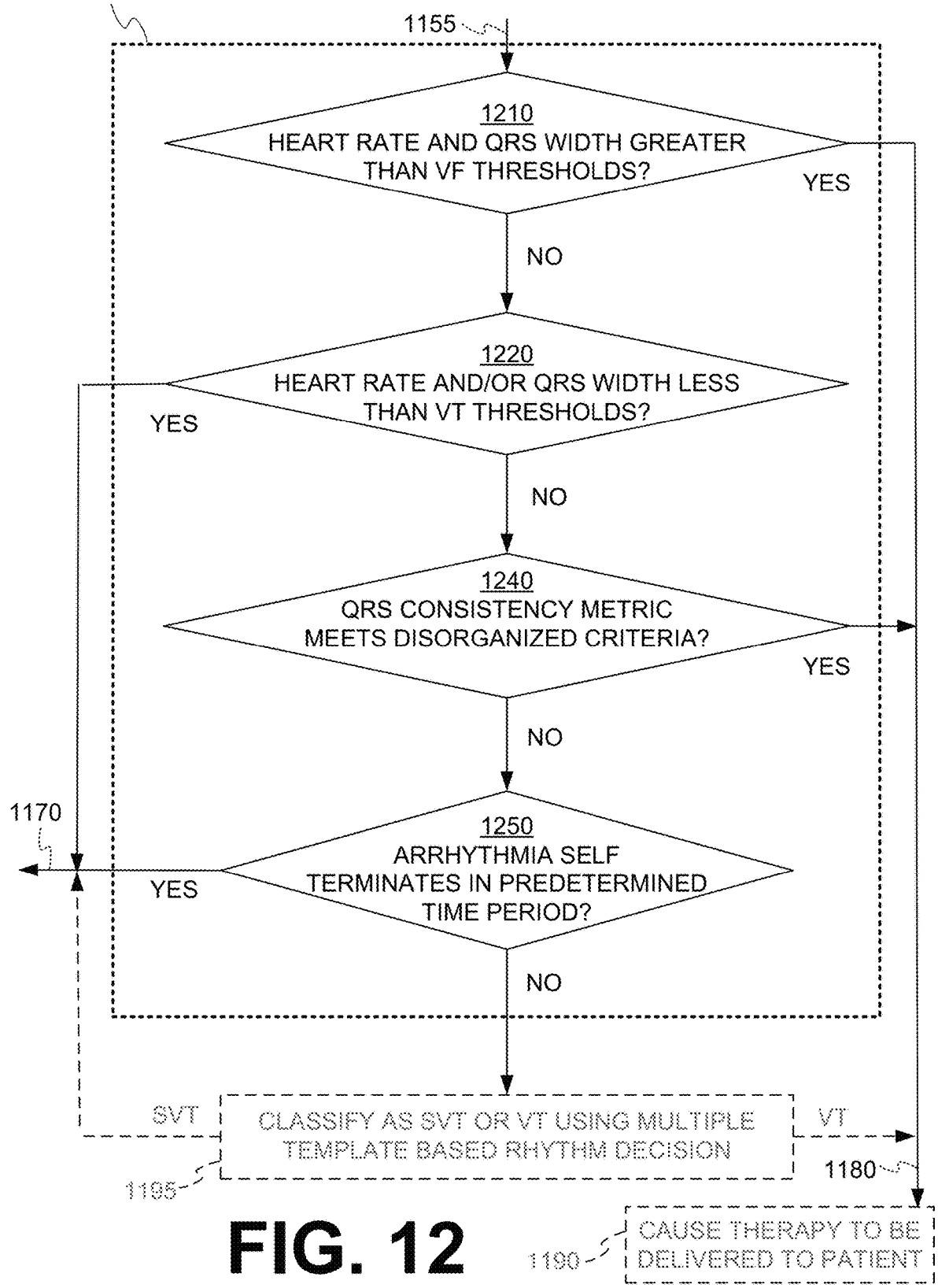
FIG. 12 is a flowchart for illustrating sample methods for implementing some operations depicted in FIG. 11, according to embodiments.

FIG. 12 is a flowchart for illustrating a method for implementing operations 1160A and 1160B depicted in FIG. 11, according to embodiments. In embodiments, the remaining operations illustrated in FIG. 12 can be performed at least in part by a processor such as, for example, processor 230 (FIG. 5).

In operation 1210, the HR from operation 1140 (FIG. 11) is compared to a VF threshold for HR and the QRS width from operation 1130 (FIG. 11) is compared to a VF threshold for QRS width. In some embodiments, the HR VF threshold is 200 bpm, and can range from 180 to 220 bpm in other embodiments. In some embodiments, the QRS width VF threshold is 120 ms and can range from 80 to 200 ms in other embodiments. If at least one of the HR and QRS width exceed their respective VF thresholds, the operational flow proceeds to a therapy process (e.g., operation 1190 in FIG. 11) in which a defibrillation shock may be delivered to the patient does not abort or divert the shock. However, if the HR and the QRS width both do not exceed their respective VF thresholds, operational flow proceeds to an operation 1220.

In operation 1220, the HR and the QRS width from operation 1130 (FIG. 11) are compared to HR and QRS width thresholds for VT. As previously described, these thresholds can be used to a define VT zone such as illustrated, for example, in FIGS. 7 and 10. If the HR and QRS width are both less than the HR VT threshold and the QRS width VT threshold, the operational flow returns to operation 1110 (FIG. 11) as indicated by arrow 1170. However, if one or both of the HR and QRS width exceed the HR VT threshold and the QRS width VT threshold, the operational flow proceeds to an operation 1240.

In operation 1240, the QRS consistency metric from operation 1150 (FIG. 11) is compared to "disorganized" criteria. In some embodiments, the disorganized criteria is as described in aforementioned U.S. patent application Ser. No. 16/554,410 entitled "METHODS AND SYSTEMS FOR DISTINGUISHING VT FROM VF". If the QRS consistency metric does meet this criteria, the operational flow proceeds as shown by arrow 1180 to therapy process such as described for operation 1190 (FIG. 11). However, if the QRS consistency metric does not meet this criteria, the operational flow proceeds to operation 1195 (FIG. 11) to be classified as SVT or VT based on posture dependent templates if the arrhythmia does not self-terminate within a predetermined time period (operation 1250).

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardiac monitoring system for a patient, the wearable cardiac monitoring system comprising:
   a memory configured to store at least one template classified as a supraventricular rhythm of the patient;
   a plurality of electrodes;
   a support structure configured to be attached to the patient and structured to position the plurality of electrodes to contact a body of the patient while the support structure is on the patient;
   a heart rate detector; and
   one or more processors configured to:
   monitor the patient's heart rhythm, wherein monitoring the patient's heart rhythm comprises:
   receive at least one output signal from the heart rate detector,
   determine a heart rate using the at least one output signal from the heart rate detector,
   receive at least one electrocardiogram (ECG) signal over each of a plurality of ECG channels via the plurality of electrodes, and
   determine whether a ventricular tachycardia (VT) threshold is met based at least in part on the determined heart rate;
   determine whether a supraventricular tachycardia (SVT) threshold for the patient is met for the plurality of ECG channels using a voting scheme based on a correlation of the received ECG signal for each of the plurality of ECG channels and the at least one template; and
   responsive to the SVT threshold for the patient being met, issue an alert.

2. The cardiac monitoring system of claim 1, in which the heart rate detector is configured to determine the patient's heart rate based at least in part on the received ECG signal.

3. The cardiac monitoring system of claim 1, wherein the one or more processors is further configured to:
   determine whether a ventricular fibrillation (VF) threshold is met based at least in part on the determined heart rate, the VF threshold being greater than the VT threshold; and
   issue an alert when the VF threshold is met.

4. The cardiac monitoring system of claim 1, wherein the system further comprises:
   an energy storage module configured to be coupled to the support structure, to receive an electric charge from the power source, and to store the received electric charge; and
   a discharge circuit coupled to the energy storage module, the discharge circuit controllable to discharge an electric charge stored in the energy storage module while the support structure is worn by the patient; and
   wherein the processor is further configured to:
   responsive to the SVT threshold for the patient being met, classify the patient's rhythm as not shockable;
   determine whether a delay shock criterion is met based on at least the VT threshold being met and the SVT threshold for the patient not being met, and
   responsive to a determination that the delay shock criterion is met, cause at least some of the stored electrical charge to be discharged through at least one of the plurality of electrodes to deliver therapy to the patient.

5. The cardiac monitoring system of claim 4, in which the one or more processors is further configured to:
   identify QRS complexes of the received ECG signal and determine a width of the identified QRS complexes; and determine whether a width threshold is met based at least in part on the determined width.

6. The cardiac monitoring system of claim 5, wherein determining whether the delay shock criterion is met is based at least on the received ECG signal meeting the following conditions for a predetermined time period: the VT threshold is met, the SVT threshold for the patient is not met, and the width threshold is met.

7. The cardiac monitoring system of claim 6, wherein the therapy comprises cardioversion therapy.

8. The cardiac monitoring system of claim 7, wherein cardioversion therapy comprises a synchronized shock of less energy than a defibrillation shock.

9. The cardiac monitoring system of claim 1, wherein the at least one template comprises a plurality of posture-based templates.

10. The cardiac monitoring system of claim 9, further comprising an accelerometer module configured to detect the posture of the patient while the support structure is on the patient.

11. The cardiac monitoring system of claim 9, wherein the one or more processors is (are) configured to daily update the at least one template.

12. The cardiac monitoring system of claim 1, wherein the one or more processors is (are) further configured to derive a template from the patient's electrocardiogram (ECG) that is sensed via the plurality of electrodes while the patient has a supraventricular originated rhythm and store the derived template in the memory.

13. The cardiac monitoring system of claim 12, wherein the one or more processors is further configured to:
determine whether the SVT threshold is met for each of the plurality of ECG channels; and
determine whether the SVT threshold is met for the patient at least by applying a voting scheme using each ECG channel's SVT threshold determination.

14. A method for use with a wearable cardiac monitoring system, the method comprising:
determining a heart rate (HR) using at least one output signal from a heart rate detector;
receiving at least one electrocardiogram (ECG) signal over each of a plurality of ECG channels via a plurality of electrodes;
determining whether a ventricular tachycardia (VT) threshold is met based at least in part on the determined HR;
determine whether a supraventricular tachycardia (SVT) threshold for the patient is met based on a correlation of received ECG signals using a voting scheme and at least one template; and
issue an alert when the SVT threshold is met.

15. The method of claim 14, further comprising:
determining whether a ventricular fibrillation (VF) threshold is met based at least in part on the determined heart rate, the VF threshold being greater than the VT threshold;
determining whether a VF criterion is met based at least in part in response to the VF threshold being met; and
responsive to the VF being met, issue an alert.

16. The method of claim 15, responsive to the SVT threshold not being met, classifying the patient's rhythm as VT.

17. The method of claim 16, further comprising:
issuing an alert in response to the heart rhythm being classified as VT for a predetermined time period.

18. The method of claim 15, further comprising:
determining a width of QRS complexes in the received ECG signal;
determining whether the determined width meets a QRS width threshold; and
responsive to the QRS width threshold being met and the VT threshold being met, issuing an alert.

19. The method of claim 14, in which the heart rate detector is configured to determine the patient's heart rate based at least in part on the received ECG signal.

20. The method of claim 14, wherein the method further comprises:
determining whether the SVT threshold is met for each of the plurality of ECG channels; and
determining whether the SVT threshold is met for the patient at least by applying a voting scheme using each ECG channel's SVT threshold determination.

\* \* \* \* \*